United States Patent
Hoffman et al.

(10) Patent No.: US 10,905,698 B1
(45) Date of Patent: Feb. 2, 2021

(54) METHODS OF TREATING SARS-COV-2 INFECTIONS

(71) Applicant: Tyme, Inc., Bedminster, NJ (US)

(72) Inventors: Steven Hoffman, Mahwah, NJ (US); John Rothman, Lebanon, NJ (US)

(73) Assignee: Tyme, Inc., Bedminster, NJ (US)

( * ) Notice: Subject to any disclaimer, the term of this patent is extended or adjusted under 35 U.S.C. 154(b) by 0 days.

(21) Appl. No.: 16/921,071

(22) Filed: Jul. 6, 2020

Related U.S. Application Data

(60) Provisional application No. 63/024,541, filed on May 14, 2020.

(51) Int. Cl.
| | | |
|---|---|---|
| *A61K 31/575* | (2006.01) | |
| *A61K 9/00* | (2006.01) | |
| *A61P 31/14* | (2006.01) | |
| *A01N 45/00* | (2006.01) | |

(52) U.S. Cl.
CPC ............ *A61K 31/575* (2013.01); *A01N 45/00* (2013.01); *A61K 9/007* (2013.01); *A61K 9/0053* (2013.01); *A61P 31/14* (2018.01)

(58) Field of Classification Search
CPC .................................................. A61K 31/575
See application file for complete search history.

(56) References Cited

U.S. PATENT DOCUMENTS

2017/0266206 A1* 9/2017 Li ................... A61K 31/585

FOREIGN PATENT DOCUMENTS

CN      106031731      * 10/2016

OTHER PUBLICATIONS

Hassan et al., American Journal of Respiratory and Critical Care Medicine, 2015, vol. 191, Supp. Meeting Abstracts, Abstract No. A4050.*

* cited by examiner

*Primary Examiner* — Rei Tsang Shiao

(74) *Attorney, Agent, or Firm* — BakerHostetler

(57) ABSTRACT

The disclosure is directed to methods of using TUDCA, or a pharmaceutically acceptable salt thereof, or a derivative thereof, for the treatment of SARS-CoV-2 infections.

13 Claims, No Drawings

US 10,905,698 B1

METHODS OF TREATING SARS-COV-2 INFECTIONS

CROSS REFERENCE TO RELATED APPLICATIONS

This application claims the benefit of U.S. Provisional Application No. 63/024,541, filed May 14, 2020, the entirety of which is incorporated by reference herein.

TECHNICAL FIELD

The disclosure is directed to methods of using TUDCA, or a salt thereof, and derivatives thereof, for the treatment and prevention of SARS-CoV-2 infections.

BACKGROUND

SARS-CoV-2 infections are a threat to public health. Treatments for SARS-CoV-2 infections, as well as treatments for COVID-19, the disease caused by the SARS-CoV-2 virus, are needed.

SUMMARY

The disclosure is directed to methods of treating a SARS-CoV-2 infection in a subject in need of treatment comprising administering to the subject a therapeutically effective amount of an agent that is TUDCA, or a pharmaceutically acceptable salt thereof, or a derivative thereof.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

As used in the specification including the appended claims, the singular forms "a," "an," and "the" include the plural, and reference to a particular numerical value includes at least that particular value, unless the context clearly dictates otherwise.

When a range of values is expressed, an exemplary embodiment includes from the one particular value and/or to the other particular value. All ranges are inclusive and combinable. Further, reference to values stated in ranges includes each and every value within that range. When values are expressed as approximations, by use of the preposition "about," it will be understood that the particular value forms another embodiment. The term "about" as used herein when referring to a measurable value such as an amount, a temporal duration, and the like, is meant to encompass reasonable variations of the value, such as, for example, 10% from the specified value. For example, the phrase "about 50%" can include 10% of 50, or from 45% to 55%, inclusive of 50%.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination.

As used herein, whether by itself or in conjunction with another term or terms, "pharmaceutically acceptable" indicates that the designated entity such as, for example, a pharmaceutically acceptable excipient, is generally chemically and/or physically compatible with other ingredients in a composition, and/or is generally physiologically compatible with the recipient thereof.

As used herein, whether by themselves or in conjunction with another term or terms, "subject(s)," "individual(s)," and "patient(s)", refer to mammals, including humans. The term human(s) refers to and includes, a human child, adolescent, or adult.

As used herein, whether by itself or in conjunction with another term or terms, it should be understood that the phrases "method of treating" and "method of treatment" may be used interchangeably with the phrase "for use in the treatment of" a particular disease.

As used herein, whether by themselves or in conjunction with another term or terms, "treats," "treating," "treated," and "treatment," refer to and include ameliorative, palliative, and/or curative uses and results, or any combination thereof. In other embodiments, the methods described herein can be used prophylactically, that is, preventatively. It should be understood that "prophylaxis" or a prophylactic use or result do not refer to nor require absolute or total prevention (i.e., a 100% preventative or protective use or result). As used herein, prophylaxis or a prophylactic (preventative) use or result refers to uses and results in which administration of a compound or composition diminishes or reduces the severity of a particular condition, symptom, disorder, or disease described herein; diminishes or reduces the likelihood of experiencing a particular condition, symptom, disorder, or disease described herein; or delays the onset or relapse (reoccurrence) of a particular condition, symptom, disorder, or disease described herein; or any combination of the foregoing.

As used herein, whether used alone or in conjunction with another term or terms, "therapeutic" and "therapeutically effective amount" refer to an amount of a compound or composition that (a) treats a particular condition, symptom, disorder, or disease described herein; (b) attenuates, ameliorates, or eliminates one or more symptoms of a particular condition, disorder, or disease described herein; (c) delays the onset or relapse (reoccurrence) of a particular condition, symptom, disorder, or disease described herein; (d) prevents the onset of a particular condition, symptom, disorder, or disease described herein. It should be understood that the terms "therapeutic" and "therapeutically effective" encompass any one of the aforementioned effects (a)-(d), either alone or in combination with any of the others (a)-(d).

As used herein, the term "alkyl", by itself or as part of another substituent, means, unless otherwise stated, a straight or branched chain hydrocarbon radical having up to twelve carbon atoms. In some embodiments, the number of carbon atoms is designated (i.e., $C_1$-$C_8$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Alkyl groups may be optionally substituted as provided herein. In some embodiments, the alkyl group is a $C_1$-$C_6$ alkyl; in some embodiments, it is a $C_1$-$C_4$ alkyl.

The term "akenyl" as used herein refers to $C_2$-$C_{12}$ alkyl group that contains at least one carbon-carbon double bond.

In some embodiments, the alkenyl group is optionally substituted. In some embodiments, the alkenyl group is a $C_2$-$C_6$ alkenyl.

The term "akynyl" as used herein refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl The term "halo," by itself or as part of another substituent, means a fluorine, chlorine, bromine, or iodine atom.

The term "alkoxy" refers to those alkyl groups attached to the remainder of the molecule via an oxygen (O) atom.

The term "thioalkyl" refers to those alkyl groups attached to the remainder of the molecule via a thio (S, SO, $SO_2$) group.

The term "cycloalkyl" as used herein refers to a 3-12 membered cyclic alkyl group, and includes bridged and spirocycles (e.g., adamantine). Cycloalkyl groups may be fully saturated or partially unsaturated. The term "cycloalkyl" also includes multiple condensed ring systems (e.g., ring systems comprising 2, 3 or 4 rings) wherein a single cycloalkyl ring (as defined above) can be condensed with one or more groups selected from heterocycles, carbocycles, aryls, or heteroaryls to form the multiple condensed ring system. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a cycloalkyl) can be at any position of the cycloalkylic ring. Examples of cycloalkyl groups include cyclopropyl, cyclobutyl, cyclopentyl, cycloheptyl, cyclohexyl, cycloheptyl, cyclooctyl, indenyl, bicyclo[2.2.1]heptanyl, bicyclo[3.1.1]heptanyl, bicyclo[4.1.0]heptanyl, spiro [3.3]heptanyl, and spiro[3.4]octanyl. In some embodiments, the cycloalkyl group is a 3-7 membered cycloalkyl.

The term "cycloalkenyl" refers to a cycloalkyl moiety having one or more double bonds, for example, cyclohexenyl, cyclopropenyl, and the like.

The term "aryl" as used herein refers to a single, all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic. Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the aromatic ring. Non-limiting examples of aryl groups include, but are not limited to, phenyl, indenyl, naphthyl, 1, 2, 3,4-tetrahydronaphthyl, and the like.

The term "aralkyl" refers to an aryl group attached to the remainder of the molecule through an alkyenyl group, for example, benzyl (phenyl-$CH_2$—)

The term "heteroaryl" as used herein refers to a single aromatic ring that has at least one atom other than carbon in the ring, wherein the atoms are selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the heteroaryl ring. It is also to be understood that the point of attachment for a heteroaryl or heteroaryl multiple condensed ring system can be at any suitable atom of the heteroaryl ring including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. Accordingly, a heterocycle (a single saturated or single partially unsaturated ring or multiple condensed ring system) has about 3-20 atoms including about 1-6 heteroatoms within the heterocycle ring system. It is also to be understood that the point of attachment of a multiple condensed ring system (as defined above for a heterocylyl) can be at any position of the heterocyclic ring. It is also to be understood that the point of attachment for a heterocycle or heterocycle multiple condensed ring system can be at any suitable atom of the heterocyclic ring including a carbon atom and a heteroatom (e.g., a nitrogen). In one embodiment the term heterocycle includes a $C_{2-20}$ heterocycle. In one embodiment the term heterocycle includes a $C_{2-7}$ heterocycle. In one embodiment the term heterocycle includes a $C_{2-5}$ heterocycle. In one embodiment the term heterocycle includes a $C_{2-4}$ heterocycle. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one. In one embodiment the term "heterocycle" refers to a monocyclic, saturated or partially unsaturated, 3-8 membered ring having at least one heteroatom. For example, the term includes a monocyclic, saturated or partially unsaturated, 4, 5, 6, or 7 membered ring having at least one heteroatom. Non-limiting examples of heterocycle include aziridine, azetidine, pyrrolidine, piperidine, piperidine, piperazine, oxirane, morpholine, and thiomorpholine. The term "9- or 10-membered heterobicycle" as used herein refers to a partially unsaturated or aromatic fused bicyclic ring system having at least one heteroatom. For example, the term 9- or 10-membered heterobicycle includes a bicyclic ring system having a benzo ring fused to a 5-membered or 6-membered saturated, partially unsaturated, or aromatic ring that contains one or more heteroatoms.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of the disclosure with one or more solvent molecules.

As used herein, the term "isomers" refers to compounds which have identical chemical constitution, but differ with regard to the arrangement of the atoms or groups in space, e.g., enantiomers, diastereomers, tautomers.

The disclosure is directed to methods of treating SARS-CoV-2 infections. According to these methods, a subject diagnosed with or suspected of having a SARS-CoV-2 infection is administered an amount of an agent that is tauroursodeoxycholic acid (TUDCA, also referred to herein as "TUDCA acid"), or a salt thereof, or derivative thereof that is therapeutically effective in treating the SARS-CoV-2 infection.

Without wishing to be bound to any particular theory, it is believed that TUDCA and its derivatives can treat SARS- CoV-2 infections by inhibiting viral replication. TUDCA and its derivatives are hydrophilic bile acids that can inhibit viral replication by disrupting the membrane functions of a SARS-CoV-2 virus, disrupting the chaperone function of heatshock proteins while providing alternative chaperone functionality, stabilizing a dysregulated endoplasmic reticulum, influencing mechanisms of protein folding, and/or facilitating the lipidation of cofactors required for autophagy of virus-infected cells, and/or inhibiting the overall availability or utility of cellular lipids for the purpose of replicating new viral particles.

TUDCA and its derivatives are water soluble. When administered, either parenterally, via inhalation, or orally, in the form of a dosage form including one or more pharmaceutically acceptable excipients, TUDCA and its derivatives are readily absorbed and distributed throughout the body, including the central nervous system.

TUDCA is known in the art and has the following formula:

TUDCA

[Chemical structure of TUDCA]

In preferred embodiments, the agent used in the methods of the disclosure is TUDCA. In other embodiments, the agent used in the methods of the disclosure is a pharmaceutically acceptable salt of TUDCA, for example sodium TUDCA.

TUDCA derivatives are also within the scope of the disclosure. Preferred TUDCA derivatives are compounds that are not TUDCA (or a pharmaceutically acceptable salt thereof) and that are of Formula I:

(I)

[Chemical structure of Formula I]

wherein
X is O or S;
$R^1$ is H, $C_{1-6}$alkyl, $C_{1-6}$haloalkyl, $C_{3-8}$cycloalkyl, $C_{3-8}$cycloalkenyl, $C_{1-6}$arlkyl, aryl, heteroaryl bound through a carbon atom, or heterocycle bound through a carbon atom;
$R^2$ is H, $C_{1-6}$alkyl, $C_{3-8}$cycloalkyl, $C_{3-8}$cycloalkenyl, $C_{1-6}$arlkyl, aryl, heteroaryl bound through a carbon atom, or heterocycle bound through a carbon atom;
$R^3$ to $R^{11}$ are, independently, H, CN, OH, $NO_2$, $N(R^A)_2$, halo, $C_{1-6}$alkyl, $C_{2-6}$alkenyl, $C_{2-6}$alkynyl, $C_{1-6}$haloalkyl, $C_{1-6}$alkoxy, $C_{1-6}$thioalkyl, $C_{3-8}$cycloalkyl, $C_{3-8}$cycloalkenyl, $C_{1-6}$arlkyl, aryl, heteroaryl, heterocycle, —OC(O)$R^A$, —C(O)$R^A$, C(O)O$R^A$, —OC(O)N($R^A$)$_2$, —C(O)N($R^A$)$_2$, —N($R^A$)C(O)O$R^A$, —N($R^A$)C(O)$R^A$, —N($R^A$)C(O)N($R^A$)$_2$, —N($R^A$)S(O)$_2R^A$, —S(O)O$R^A$, —S(O)$_2$O$R^A$, —S(O)N($R^A$)$_2$, —S(O)$_2$N($R^A$)$_2$, or PO$_3$($R^A$)$_2$;
each $R^A$ is, independently, H, OH, $C_{1-6}$alkyl, $C_{3-8}$cycloalkyl, $C_{1-6}$arlkyl, aryl, heteroaryl, or heterocycle;
or a pharmaceutically acceptable salt, solvate, or isomer thereof.

According to the described methods, the agent, preferably TUDCA or a pharmaceutically acceptable salt of TUDCA, is administered to the subject. In some aspects, the agent is administered parenterally. In other aspects, the agent is administered via inhalation. In preferred aspects, the agent is administered orally.

The amount of agent administered to the subject will be the amount effective in treating the SARS-CoV-2 infection as described more fully herein. For example, in some aspects, up to 5 g/day, up to 4 g/day, up to 3 g/day, up to 2 g/day, up to 1 g/day, or up to 0.5 g/day of the agent (preferably TUDCA or a pharmaceutically acceptable salt of TUDCA) will be administered to the subject. In other aspects, 0.5, 1, 1.5, 2, 2.5, 3, 3.5, 4, or 4.5 g/day of the agent (preferably TUDCA or a pharmaceutically acceptable salt of TUDCA) will be administered to the subject.

In some aspects, the subject has been diagnosed with COVID-19. In other aspects, the subject is suspected of having COVID-19. In other aspects, the subject intends to prevent the contracting of COVID-19.

In some aspects, the agent is administered prior to the subject presenting with a symptom of COVID-19. In other aspects, the agent is administered to the subject after the subject has presented with a symptom of COVID-19.

In some aspects, the agent is administered to the subject prior to the detection of any SARS-CoV-2 in a body fluid (e.g., blood, respiratory fluid) of the subject. In other aspects, the agent is administered to the subject after SARS-CoV-2 has been detected in a body fluid of the subject.

In some aspects, the agent is administered to the subject for 1 day to 90 days. In some aspects, the agent is administered to the subject for 1 day to 60 days. In some aspects, the agent is administered to the subject for 1 day to 30 days. In some aspects, agent is administered to the subject for 1 day to 14 days. In some aspects, the agent is administered to the subject for 1 day to 7 days. In some aspects, the agent is administered for 7 days. In some aspects, the agent is administered for 14 days. In some aspects, the agent is administered for 21 days. In some aspects, the agent is administered for 28 days. When used prophylactically, the agent is administered daily for as long as the risk of infection persists.

The daily amount of the agent can be orally administered to the subject in one dose or in divided doses throughout the day. In some aspects, the agent is administered once a day. In other aspects, the agent is administered twice a day. In yet other aspects, the agent is administered three times a day. Preferably, the agent is administered once per day or twice per day or three times per day.

In some aspects of the disclosure, the agent is administered to the subject and the administration reduces the risk that the subject will become infected with SARS-CoV-2 after exposure to the SARS-CoV-2 virus. In some aspects of the disclosure, the agent is administered to the subject and the administration reduces the risk that the subject will develop COVID-19 after exposure to the SARS-CoV-2 virus.

In some aspects, administration of an agent according to the disclosure results in an improvement in one or more of the subject's SARS-CoV-2 infection symptoms, as compared to the subject's baseline SARS-CoV-2 infection symptoms. SARS-CoV-2 infection symptoms can vary, depending on the particular subject. SARS-CoV-2 infection symptoms can include, e.g., fever, rigors, decreased oxygen saturation, shortness of breath, difficulty breathing, fatigue, muscles aches, body aches, chest pain or pressure, headache, new loss of taste, new loss of smell, sore throat, congestion, nausea, vomiting, diarrhea, confusion, cough, and rash.

In some aspects of the disclosure, the administration of the agent results in a reduction of the subject's fever. In other aspects, the administration of the agent results in a reduction in rigors experienced by the subject. In other aspects, administration of the agent results in an increase in the subject's oxygen saturation. In other aspects, administration of the agent results in a reduction in the subject's fatigue. In other aspects, administration of the agent results in a lessening of the frequency and/or severity of the subject's coughing. In other aspects, administration of the agent results in a lessening of the subject's rash.

In some aspects, the administration of the agent results in a reduction in the subject's viral load. Methods for determining viral load are known in the art and include using PCR.

In some aspects, the administration of the agent results in an improvement in the subject's clinical status. Clinical status can be determined by those of skill in the art using the WHO Ordinal Scale for Clinical Improvement, shown below.

| Score | Descriptor | Patient State |
|---|---|---|
| 0 | No clinical or virologic evidence of infection | Uninfected |
| 1 | No limitation of activities | Ambulatory |
| 2 | Limitation of activities | Ambulatory |
| 3 | Hospitalized, no oxygen therapy | Hospitalized Mild Disease |
| 4 | Oxygen by mask or nasal prongs | Hospitalized Mild Disease |
| 5 | Non-invasive ventilation or high-flow oxygen | Hospitalized Severe Disease |
| 6 | Intubation and mechanical ventilation | Hospitalized Severe Disease |
| 7 | Ventilation + additional organ support - pressors, RRT, ECMO | Hospitalized Severe Disease |
| 8 | Death | Dead |

In some aspects, the administration results in an improvement in the subject's clinical status, as represented as a reduction in the subject's WHO Ordinal Scale of 1 point. In some aspects, the administration results in a reduction in the subject's WHO Ordinal Scale of 2 points. In some aspects, the administration results in a reduction in the subject's WHO Ordinal Scale of 3 points. In some aspects, the administration results in a reduction in the subject's WHO Ordinal Scale of 4 points. In some aspects, the administration results in a reduction in the subject's WHO Ordinal Scale of 5 points. In some aspects, the administration results in a reduction in the subject's WHO Ordinal Scale of 6 points.

In some aspects, the agent can be used to inactivate SARS-CoV-2 present in air so as to decrease the infectiousness of the SARS-CoV-2 in the air. In some aspects, the agent can be used to inactivate SARS-CoV-2 present on surfaces so as to decrease the infectiousness of the SARS-CoV-2 on the surfaces.

The following examples are provided to illustrate some of the concepts described within this disclosure. While each example is considered to provide specific individual embodiments of disclosure, none of the Examples should be considered to limit the more general embodiments described herein. In the following examples, efforts have been made to ensure accuracy with respect to numbers used but some experimental error and deviation should be accounted for.

EXAMPLES

Example 1

The study is of TUDCA for treating a SARS-Co-V-2 infection. Following initial assessment of a subject, the subject's baseline viral load, viral infection symptoms, and clinical status will be documented. Subjects will be assigned to one of two treatment arms.

Arm A: TUDCA in addition to standard of care. TUDCA to be administered as 500 mg capsules, b.i.d., for up to 90 days.

Arm B: placebo, in addition to standard of care.

Efficacy will be analyzed based on one or more endpoints including, for example
change in clinical status using WHO Ordinal Scale
length of time to resolution of fever
length of time to normalization of oxygen saturation
overall survival
rate of non-elective mechanical ventilation
duration of mechanical ventilation
number of ICU days
any other criteria deemed relevant Example 2

Thirteen rescue squad members servicing a New Jersey hospital facility between March 2020 and May 2020 were provided with TUDCA gelatin capsules (500 mg, powder in capsule) and instructed to administer one capsule, twice per day, for the duration of the COVID-19 epidemic.

Prior to initiating TUDCA administration, one member tested positive for SARS-CoV-2 and presented with COVID-19 symptoms. After twice daily TUDCA, the member's health returned to normal.

None of the other twelve members have presented with COVID-19 symptoms, despite repeated exposure to COVID-19 patients over at least 3 months.

Example 3

A subject presenting with COVID-19 symptoms was instructed to administer one gelatin capsule of TUDCA (500 mg, powder in capsule), twice per day. After twice daily TUDCA administration, the subject's health returned to normal.

Example 4

The study was to determine if commercial TUDCA (commercially available, manufactured in China), TUDCA acid (reagent grade, Sigma-Aldrich Inc.), or sodium TUDCA (reagent grade, Sigma-Aldrich Inc.) inhibit the growth of SARS-CoV-2 in vitro. USA-WA1/2020 strain of the virus was used, acquired from BEI Resourced. This was propagated in Vero E6 cells (ATCC CRL-1586); these cells were also used for the neutralization assay. Vero E6 cells were cultured in growth media consisting of Dulbecco's Modified Eagle Medium/F12 (DMEM/F12) supplemented with 5% FBS, and PSN (penicillin, streptomycin, and neomycin).

The Vero E6 cells were plated on 96-well plates the day before the assay and were allowed to grow to ~60% confluence. All three drugs were reconstituted with DMSO to a concentration of 100 mg/mL. That was further diluted in DMEM/F12 to 5 mg/mL. TUDCA came out of solution that this point but the next 1:2 dilution was soluble and both were used in the plate. A 1:2 serial dilution series was performed to examine final concentrations of 1.25, 0.625, 0.31, 0.156, 0.078, 0.039, and 0.02 mg/mL. DMSO controls were used to account for DMSO concentrations at 1.25, 0.625, 0.31, 0.156, 0.078, 0.039, and 0.02%. Dilutions were pre-incubated with virus for 60 minutes prior to addition to cells. This was to allow drug to interact with virus prior to virus infection. Additionally, drug and virus were added to Vero cells simultaneously. 45 minutes after virus addition, DMEM/F12+FBS was added to feed the cells. The assay was executed in five replicates for each condition. Test wells received approximately 100 TCID50/well of SARS-CoV-2. Growth of the Vero E6 cells was observed and monitored for cytopathic effects (CPE) associated with successful virus replication. All wells were examined on Day 2 and Day 4 post-infection.

Cytotoxicity was seen in commercial TUDCA wells at 1.25 and 0.625 mg/mL final concentrations. Slowed cell growth was seen in 1.25 mg/mL of TUDCA acid and sodium TUDCA as well as corresponding DMSO controls (1.25%). Cytotoxicity was attributed to DMSO. Day 2 reads showed no CPE in 1.25 mg/mL of TUDCA acid and sodium TUDCA for both viral preincubation and simultaneous addition. Day 4 reads showed no CPE in 1.25 mg/mL of TUDCA acid and sodium TUDCA for simultaneous addition tests. Results are summarized in Table 1 for 1.25 mg/mL concentrations and corresponding DMSO controls. Both TUDCA acid and sodium TUDCA had an EC50 of 0.98 mg/ml as calculated by the Quest Graph™ EC50 Calculator from AAT Bioquest, Inc. All uninfected controls remained healthy and did not display any CPE throughout the 4-day observation period. The back titer was consistent with previous virus growth results.

TABLE 1

Results for Day 2 and Day 4 drugs at 1.25 mg/mL

|  |  | Day 2 CPE | Day 2 Cytotoxicity | Day 4 CPE | Day 4 Cytotoxicity |
|---|---|---|---|---|---|
| Simultaneous addition | TUDCA | CPE in 5/5 wells | Cytotoxicity in 5/5 wells | CPE in 5/5 wells | Cytotoxicity in 4/5 wells |
|  | TUDCA acid | No CPE in 5/5 wells | Minimal cytotoxicity in 5/5 wells | No CPE in 4/5 wells | No cytotoxicity in 5/5 wells |
|  | Sodium TUDCA | No CPE in 5/5 wells | Minimal cytotoxicity in 5/5 wells | No CPE in 5/5 wells | No cytotoxicity in 5/5 wells |
|  | DMSO | CPE in 5/5 wells | Minimal cytotoxicity in 5/5 wells | CPE in 5/5 wells | No cytotoxicity in 5/5 wells |
| Pre-Incubation with Virus | TUDCA | CPE in 5/5 wells | NA | CPE in 5/5 wells | NA |
|  | TUDCA acid | No CPE in 5/5 wells | NA | CPE in 5/5 wells | NA |
|  | Sodium TUDCA | No CPE in 5/5 wells | NA | No CPE in 5/5 wells | NA |
|  | DMSO | CPE in 5/5 wells | NA | CPE in 5/5 wells | NA |

This experiment demonstrated that at 1.25 mg/mL, TUDCA acid and sodium TUDCA inhibit SARS-CoV-2 infection of Vero cells when dosed simultaneously with viral addition to cells. TUDCA acid and sodium TUDCA both have a calculated EC50 of 0.98 mg/mL.

What is claimed is:

1. A method of treating COVID-19 in a subject in need thereof comprising administering to the subject a therapeutically effective amount of an agent that is tauroursodeoxycholic acid (TUDCA), or a pharmaceutically acceptable salt thereof.

2. The method of claim 1, wherein the agent is TUDCA.

3. The method of claim 1, wherein the agent is sodium TUDCA.

4. The method of claim 1, wherein the agent is administered orally.

5. The method of claim 1, wherein the agent is administered parenterally.

6. The method of claim 1, wherein the agent is administered via inhalation.

7. The method of claim 1, wherein the amount of the agent administered to the subject is up to 5 g/day.

8. The method of claim 1, wherein the agent is administered twice per day.

9. The method of claim 1, wherein the administration results in a reduction in the subject's SARS-CoV-2 viral load.

10. The method of claim 1, wherein the administration results in an improvement in one or more of the subject's viral infection symptoms.

11. The method of claim 1, wherein the administration results in an improvement in the subject's clinical status.

12. The method of claim 1, wherein the agent is administered after the subject is presenting a symptom of COVID-19.

13. The method of claim 1, wherein the agent is administered prior to the subject presenting a symptom of COVID-19.

* * * * *